United States Patent [19]
Tóth et al.

[11] 4,039,589
[45] Aug. 2, 1977

[54] α-SUBSTITUTED BENZHYDROL DERIVATIVES AND A PROCESS FOR THE PREPARATION THEREOF

[75] Inventors: Edit Tóth; József Törley; Szabolcs Szeberényi; Éva Pálosi; László Szporny; Sándor Görög; Csilla Mészáros, all of Budapest, Hungary

[73] Assignee: Richter Gedeon Vegyeszeti Gyar Rt., Budapest, Hungary

[21] Appl. No.: 495,847

[22] Filed: Aug. 8, 1974

[30] Foreign Application Priority Data

Aug. 15, 1973 Hungary .................................. RI 521

[51] Int. Cl.² ............................................. C07C 31/16
[52] U.S. Cl. .............................. 260/618 B; 260/570.7; 260/570.9; 260/578; 260/465 F; 260/293.79; 260/609 F; 260/520 C; 260/558 P; 424/345
[58] Field of Search ........................................ 260/618 B

[56] References Cited

U.S. PATENT DOCUMENTS

| 2,430,586 | 11/1947 | Ruthruff et al. | 260/618 B |
| 3,106,587 | 10/1963 | Harms | 260/618 B |
| 3,169,962 | 2/1965 | Yale et al. | 260/618 B |

FOREIGN PATENT DOCUMENTS

| 1,507,192 | 11/1967 | France | 260/618 B |

OTHER PUBLICATIONS

C.A. 57:9714 h (1962) Bercot et al.
C.A. 65:3797 c (1966) Lafon.
C.A. 60:1123 g (1964) Koerbl et al.
J. Pharm. Sci. 59:1042–1043 (1970), Murty et al.
J. Sci. & Ind. Research 21 B:374–377 (1962), Thaker et al.

Primary Examiner—Norma S. Milestone
Attorney, Agent, or Firm—Karl F. Ross; Herbert Dubno

[57] ABSTRACT

A compound of the formula:

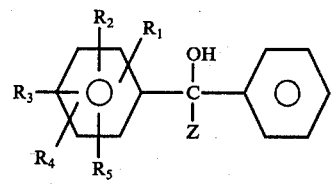

wherein
Z is ethyl or vinyl,
$R_1$ and $R_2$ are hydrogen, lower alkyl, lower alkenyl or trihalomethyl,
$R_3$ and $R_4$ are hydrogen, lower alkyl, lower alkenyl, trihalomethyl, cyclopentyl, benzyl or phenyl, and
$R_5$ is lower alkyl, lower alkenyl, trihalomethyl, cyclopentyl, benzyl, or phenyl with the proviso that where $R_1$, $R_2$, $R_3$ and $R_4$ each is hydrogen, $R_5$ is not methyl attached to the 4-position of the benzene ring, or a pharmaceutically acceptable acid addition or quaternary ammonium salt thereof is disclosed as effective in the regulation of the liver microsomal enzyme system.

4 Claims, No Drawings

α-SUBSTITUTED BENZHYDROL DERIVATIVES AND A PROCESS FOR THE PREPARATION THEREOF

This invention relates to pharmaceutically active new α-substituted benzhydrol derivatives.

The new compounds according to the invention correspond to the formula (I)

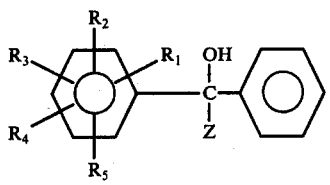

wherein

Z is an ethyl or vinyl group, and, when Z is ethyl, $R_1$ and $R_2$ each is hydrogen, halogen, a straight-chained or branched, saturated or unsaturated lower aliphatic hydrocarbon group, a trihalomethyl, nitro, nitrile group, an etherified non-etherified, an esterified or non-esterified hydroxy or hydroxyalkyl group, an esterified or non-esterified carboxy group, an acylated or non-acylated amino or lower aminoalkyl group, a lower alkylamino group or an esterified non-esterified, an etherified or non-etherified mercapto group, $R_3$ and $R_4$ each is hydrogen, halogen, a straight-chained or branched, saturated or unsaturated lower aliphatic hydrocarbon group, a cycloalkyl group, an aralkyl or aryl group, a trihalomethyl group, nitro group, nitrile group, an non-etherified, an etherified esterified or non-esterified hydroxy or hydroxyalkyl group, an esterified or non-esterified carboxy group, an acylated or non-acylated amino or lower aminoalkyl group, a mono- or di-lower alkylaminoalkyl group forming a chain or a ring through a carbon, nitrogen or oxygen atom, a lower alkylamino-mono- or di-lower alkyl group, forming a chain or a ring through a carbon, nitrogen or oxygen atom, or an esterified, and non-esterified an etherified or non-etherified mercapto group, and $R_5$ is halogen, a straight-chained or branched, saturated or unsaturated $C_{2-6}$ aliphatic hydrocarbon group or cycloalkyl group, an aralkyl or aryl group, a trihalomethyl group, nitro group, nitrile group, an etherified or non-etherified, an esterified or non-esterified hydroxy or hydroxyalkyl group, an esterified or non-esterified carboxy group, an acylated or non-acylated amino or lower aminoalkyl group, a mono- or di-lower alkylamino group forming a chain or a ring through a carbon, nitrogen or oxygen atom, a lower alkylamino-mono- or di-lower alkyl group forming a chain or a ring through a carbon, nitrogen or oxygen atom, or an esterified non-esterified, an etherified or non-etherified mercapto group, with the proviso that i. when $R_1$, $R_2$, $R_3$ and $R_4$ each is hydrogen, $R_5$ is not an amino or dimethyl-amino group attached to position 2 or 4, a 1-pyrrolidinyl group attached to position 2, or a methyl or methoxy group or bromine atom attached to position 4, or ii. when $R_1$, $R_2$ and $R_3$ each is hydrogen, $R_4$ and $R_5$ may not represent a 2,4-dimethoxy or 3,4-dimethoxy group, or iii. when $R_1$ and $R_2$ each is hydrogen, $R_3$, $R_4$ and $R_5$ may not represent a 2,4,5-trimethoxy, a 2,4,6-trimethoxy, a 4-methoxy-3,5-dimethyl or 2-amino-3,5-dibromo group, or when Z stand for vinyl $R_1$ and $R_2$ each stand for hydrogen, halogen a straight-chained or branched, saturated or unsaturated lower aliphatic hydrocarbon group, a trihalomethyl, nitro, nitrile group, an etherified non-etherified, an esterified or non-esterified hydroxy or hydroxyalkyl group, an esterified or non-esterified carboxy group, an acylated or non-acylated amino or lower aminoalkyl group, a lower alkylamino group or an esterified non-esterified, an etherified or non-etherified mercapto group, $R_3$, $R_4$ and $R_5$ each is hydrogen, halogen, a straight-chained or branched, saturated or unsaturated lower aliphatic hydrocarbon group or a cycloalkyl group, an aralkyl or aryl group, a trihalomethyl group, nitro group, nitrile group, an etherified non-etherified, an esterified or non-esterified hydroxy or hydroxyalkyl group, an esterified or non-esterified carboxy group, an acylated or non-acylated amino or lower aminoalkyl group, a mono- or di-lower alkylamino group forming a chain or a ring through a carbon, nitrogen or oxygen atom, a lower alkylamino mono- or di-lower alkyl group, forming a chain or a ring through a carbon, nitrogen or oxygen atom, or an esterified non-esterified, an etherified or non-etherified mercapto group, with the proviso that if $R_1$, $R_2$, $R_3$ and $R_4$ each is hydrogen, $R_5$ cannot be hydrogen or 4-methyl group.

The term "halogen" used in connection with $R_1$, $R_2$, $R_3$, $R_4$ and $R_5$ embraces all of the halogens, and may be e.g. fluorine, chlorine, bromine or iodine.

The straight-chained or branched, saturated or unsaturated alkyl groups are preferably those containing from 1 to 6 carbon atoms, such as methyl, ethyl, n-propyl, iso-propyl, n-butyl, isobutyl, tert-butyl, amyl, iso-amyl, hexyl, isohexyl, vinyl, allyl, propenyl, butenyl, pentenyl, hexenyl and propargyl. Of these groups methyl, n-butyl and tert-butyl are the most preferred.

The cycloalkyl groups are preferably mono-or polycyclic groups with 5 to 10 carbon atoms, such as cyclopentyl, cyclohexyl, cycloheptyl, etc. The most preferred cycloalkyl group is cyclopropyl.

The term "aralkyl" refers to mono- or polycyclic groups containing from 7 to 20 carbon atoms, preferably mono- or polycyclic aryl-(lower alkyl)-groups, such as a benzyl, phenethyl, phenylpropyl, phenylbutyl, naphthylmethyl, naphthylethyl, naphthylpropyl or naphthylbutyl group. Of these groups benzyl is the most preferred.

The aryl groups are preferably mono- or polycyclic aromatic hydrocarbon groups containing from 6 to 14 carbon atoms, such as the phenyl, diphenyl or naphthyl group, particularly the phenyl group.

The trihalomethyl groups may contain any of the halogens mentioned above, but is preferably trifluoromethyl.

The hydroxyalkyl groups may be those derived from any of the alkyl groups listed above. Both the hydroxy and the hydroxyalkyl groups may occur in etherified or esterified forms. As an example of the esterified groups, those acylated with an aliphatic or aromatic carboxylic acyl group are to be mentioned.

The acyl groups derived from aliphatic carboxylic acids may be e.g. those derived from staturated monocarboxylic acids, such as formic acid, acetic acid, propionic acid, isomeric butyric acids, isomeric valeric acids, or those derived from unsaturated monocarboxylic acids, such as acrylic acid, crotonic acid, vinylacetic acid, methacrylic acid, etc.

Of the acyl groups derived from aromatic carboxylic acids, e.g. those derived from benzoic acid, various diphenylcarboxylic acids and various naphthoic acids are to be mentioned.

The etherified hydroxy group may be preferably a lower alkoxy group, containing as the alkyl moiety any of the above-mentioned alkyl groups, but preferably methyl or ethyl.

The carboxy group may be esterified with an aliphatic or aromatic alcohol, such as ethanol, methanol, n-propanol, isopropanol, n-butanol, isobutanol, tert-butanol, isomeric pentanols, isomeric hexanols, benzylalcohol, isomeric phenethylalcohols, etc.

The aminoalkyl group may contain any of the alkyl groups mentioned above, and may be acylated with the acyl groups listed above.

The amino group may be acylated with any of the acyl groups listed above. A preferred representative of the acylamino groups is N-benzoylamino.

The lower alkylamino, dialkylamino, alkylaminoalkyl and dialkylaminoalkyl groups may contain any of the alkyl groups listed above, but they contain preferably as ethyl group as the alkyl moiety. When joined together through a carbon, nitrogen or oxygen atom, these groups also form a preferably 5 to 7 membered saturated ring system. Of these cyclic groups e.g. pyrrolidino, piperidino, perhydroazepinyl, pyrazolidino, imidazolidino, piperazino, hexahydropyrimidino, hexahydro-pyridazinyl, hexahydro-diazepinylr, oxazolidinyl and morpholino groups are mentioned. The most preferred cyclic group is piperidino.

The mercapto group may be esterified with the acyl groups mentioned at the esterified hydroxy group, or may be etherified with alkyl groups. A preferred representative of the functional mercapto groups is methylmercapto.

The pharmaceutically effective acid addition salts and quaternary ammonium salts of these compounds are also included by the scope of the invention.

The new compounds of the formula (I) and their salts possess valuable pharmacological properties. More particularly, these compounds exert a blocking or inducing effect, respectively, on the foreign-substance-metabolizing liver microsomal enzyme system, which enables their widespread use in therapy. Of the new compounds inhibiting the polyfunctional microsomal oxidase enzyme, e.g. 2-methoxy-α-ethylbenzhydrol, 2,4-dimethoxy-α-vinyl-benzhydrol, and 4-(β-diethyl-aminoethoxy-α-ethyl-benzhydrol are of particular value. These compounds exert a long-lasting inhibition, the degree of which remains significant even 48 hours after administration. Upon the addition of these substances the activity of the liver to metabolize xenobiotic substances (e.g. pharmaceuticals, steroids, etc.) decreases, thus both the life period and the effectivity period of these xenobiotic substances is prolonged in the organism.

These new compounds listed above are superior to (2-diethylaminoethyl)-αα-diphenyl-valerate (Proadiphene), postulated so far to be the most effective drug in this pharmacological domain, with respect to their activity and effectivity period. In contrast with the phenomenons observed on patients treated with (2-diethylaminoethyl)-αα-diphenyl-valerate, the activity of the enzyme system does not increase after the cessation of the blocking effect. Thus the new compounds, when combined with other therapeutically active agents, increase the effectivity period of the latter ones.

The enzyme inhibiting ability of the new compounds was tested in vivo by measuring the change of hexobarbital oxidase activity. Female Wistar rats, each weighing 80 to 100 g., were treated orally with a single 0.3 mM/kg. dosage of the active agent. 24 and 48 hours after the administration of the active agent, respectively, the animals were narcotized with a 40 mg./kg. i.v. dosage of hexobarbital sodium, and the time elapsed until complete awakening was measured (Noordhoek, J.: Eur. J. Pharmacol. 3, 242 (1968). The data were recorded, and the mean values, the standard errors, as well as the percentage increase with respect to the controls were calculated for each group. The increase of the narcosis period indicates that upon the action of the enzyme inhibiting compounds the conversion rate of hexobarbital in the organism into a biologically inactive metabolic decreases. The hexobarbital concentration of the plasma, measured on the instant of awakening, was the same for both the treated and the control animals; thus the increase of narcosis period was not due to a certain central nervous interaction (Jori, A., Bianchatti,A., Presentini, P. E.: Biochem. Pharmacol. 19, 2687(1970).

The results of the above test are summarized in Table 1.

Table 1

| Substance administered | Change of narcosis period with respect to the controls, % | | | Hexobarbital concentration at wakening |
| | 2 hours | 24 hours | 48 hours | |
| | after administration | | | 48 h., μg/100 ml. |
| --- | --- | --- | --- | --- |
| E 16 | + 43 | + 43 | + 46 | 7.1 ± 0.83 |
| E 17 | + 109 | + 28 | + 33 | 7.6 ± 0.90 |
| Proadiphene | + 175 | − 38 | − 39 | 8.1 ± 1.0 |
| Control | | | | 7.3 ± 0.92 |

E 16 = 2-methoxy-α-ethyl-benzhydrol
E 17 = 4-(β-diethylaminoethoxy)-α-ethyl-benzhydrol Both the increase of the narcosis period and the duration of the effect (the compounds being effective even 48 hours after administration!) indicate that compounds E 16 and E 17 inhibit the elimination of xenobiotic agents and the inactivation, thereof in the liver for a long time. The effect of the new compounds tested is better than that of Proadiphene also from qualitative aspects, since, in contrast with Proadiphene, the initial inhibiting effect caused by the α-substituted benzhydrols is not followed by an increased detoxicating activity.

The other group of the new compounds according to the invention possesses enzyme-inducing effect, and can be used in a wide range in therapy; thus, for example, in the treatment of neonatal jaundice. Neonatal jaundice appears when the amount or the activity of UDP-glucuronyltransferase enzyme (E.C. 2.4.1.17; an enzyme conjugating bilirubin with glucuronic acid), respectively, is insufficient to glucuronize the free bilirubin entering into the plasm upon the lysis of the red blood cells, and, since free bilirubin is not excreted with the bile or urine, either, remains steadily in the circulation and causes jaundice. The free, lipoid-soluble bilirubin is also bound to the central nervous system, inhibiting there cell respiration, thus a high bilirubin level may result in irreversible injuries and sometimes also in death. A more or less pronounced increase in the bilirubin concentration in plasma can be observed for all newborns, but, particularly due to the increase of premature births, blood group (ABO, Rh) imcompabilities, and anoxial deliveries, the ratio of endangered infants is high and steadily increasing. Therapeutical trials are carried out all over the world for the prophylaxis and treatment of neonatal jaundice. Phenobarbital, the drug used most frequently for this purpose so far, is, however, not innocuous, due to its toxic (sedative and respiration-paralyzing) side effects, and therefore an increasing interest has been arising towards components with more advantageous properties. For treatment purposes compounds exerting a strong inducing effect on the liver microsomal enzyme system and thus increasing glucuronization can be used. These compounds should, however, also meet the following requirements: able to be administered to newborns even on the first day of live, effectiveness upon oral administration, effectiveness even in a single dosage, and relatively rapid (i.e. not too retarded) effect. Moreover, these compounds should have no, or only negligible side effects and should have low toxicity values. An essential factor is that the compounds should have no effect on the central nervous system, endocrine system and immume apparatus, since these systems are highly sensitive on the first extrauterine days, and give irreversible responses to certain pharmacons.

Of the compounds according to the invention, 3-chlor-α-ethyl-benzhydral, 3-trifluoromethyl-α-ethyl-benzhydrol, 2,5-dimethyl-α-ethyl-benzhydrol, 2-fluoro-α-vinyl-benzhydrol and 2,4-dichloro-α-ethyl-benzhydrol exert a particularly advantageous inducing effect on the liver microsomal enzyme system. Both the duration and the strength of their effect reaches that of phenobarbital, but they have no central nervous effects, in contrast with the hypnotic and respiration paralyzing effects of phenobarbital. These compounds increase the activity of the liver enzymes to detoxicate (metabolize) xenobiotic substances, and within this, they increase the glucuronyl-transferase activity, thus leading to the glucuronization of bilirubin and to the removal of the same from the circulation. Besides the treatment of neonatal hyperbilirubinaemie, these compounds can also be used for the treatment of hyperbilirubineamias of various origin, and they accelerate the regeneration of the liver. Upon treatment with the new inducing agents, a rapid excretion of foreign substances — primarily insecticides — accumulated in the organism due to environmental pollution, can also be achieved. In diseases accompanied by overproduction of steroidal hormones, an increased inactivation of steroids can be achieved by the repeated administration of the enzyme inducing compounds. The new compounds according to the invention increase the inactivation of progesterone in laboratory animals, thus, when added in combination with oestrogen, they can be used for the experimental prophylaxis of pregnancy.

The enzyme-inducing potency of the new compounds was determined by several methods. One of these methods was the in vivo measurement of hexobarbital oxidase activity. This test was carried out as described above in connection with the compounds possessing blocking activity.

The decrease of narcosis period is due to the fact that the new compounds according to the invention accelerate the elimination of hexobarbital, a foreign substance, from the body. When administering the compound to be tested in a single dosage and measuring the duration of hexobarbital narcosis 24 hours after the administration, the following results are obtained:

Table 2

| Substance added | Sleeping period ± standard error | | | |
|---|---|---|---|---|
| | 5 mg./kg. | 10 mg./kg. | 20 mg./kg. | 40 mg./kg. |
| Control (27.6 ± 1.9) | 21.7 ± 2.0 | 15.2 ± | — | — |
| E 9 | 21.7 ± 2.0 | 15.2 ± 1.4 | 13.6 ± 1.4 | 12.4 ± 1.2 |
| E 11 | 22.0 ± 2.1 | 16.4 ± 1.6 | 15.0 ± 1.4 | 13.0 ± 1.2 |
| E 15 | 18.0 ± 1.7 | 14.2 ± 1.5 | 10.6 ± 1.2 | 8.8 ± 0.9 |
| E 20 | 23.8 ± 1.9 | 18.6 ± 1.9 | 14.0 ± 1.3 | 13.0 ± 1.2 |
| Phenobarbital | 20.1 ± 2.0 | 14.3 ± 1.4 | 14.0 ± 1.3 | 12.5 ± 1.2 |

E 9 = 3-chloro-α-ethyl-benzhydrol
E 11 = 2,4-dichloro-α-ethyl-benzhydrol
E 15 = 3-trifluoromethyl-α-ethyl-benzhydrol
E 20 = 2,5-dimethyl-α-ethyl-benzhydrol As the data of Table 2, shows the new compounds according to the invention are equal or superior to phenobarbital with respect to their effect shown in the above test.

The biological halving period of hexobarbital (Noordhoek, J.: Eur. J. Pharmacol. 3, 242(1968)) and the hexobarbital concentration at the instant of wakening were determined on female rats each weighing 150 g., pre-treated with the compounds to be tested 24 hours prior to the administration of hexobarbital. The results are listed in Table 3.

Table 3

| Substance | t½ min. | Concentration at wakening µg./ml. |
|---|---|---|
| Control | 37 | 6.8 ± 0.8 |
| E 11 | 26 | 7.1 ± 0.8 |
| E 15 | 23 | 7.3 ± 0.9 |

The data listed in Table 3 shows, that biological halving periods are significantly shorter in the test groups than in the control group, while the hexobarbital concentration measured in the individual groups on the instant of wakening practically does not differ from each other. Accordingly, the compounds of the formula (I) accelerate the elimination of hexobarbital from the plasma to a great extent, but, as evidenced by the unchanged hexobarbital concentration at awakening, they do not influence the sensitivity of the central nervous system towards hexobarbital. Consequently, the compounds in question act solely on the liver microsomal enzyme system, and exert an inducing activity on this enzyme system.

The biological halving period of meprobamate was determined 24 hours after pre-treatment with the compounds of the formula (I) (Ludwig, B. J., Hoffman, A. J.: Arch. Biochem. 72, 234 (1957). The results are listed in Table 4.

Table 4

| Substance | t½ (hours) |
|---|---|
| Control | 4.0 |
| E 11 | 2.8 |
| E 15 | 2.1 |

As the data of Table 4 shows, the elimination rate of meprobamate increased significantly upon pre-treatment with the compounds of the formula (I). Thus these compounds increase significantly the conversion rate of meprobamate into a biologically inactive metabolite.

The bromosulfophthaleine (BSP) concentration of the plasm was determined 24 hours after pre-treatment with the compounds of the formula (I) and after the intravenous administration of bromsulfophthaleine, respectively (Varga, F., Fischer, E.: Acta Physiol. Hung. 36, 431(1969). The results of this test are summarized in Table 5.

Table 5

| Substance | BSP μg./mg. plasma |
|---|---|
| Control | 16.9 |
| E 9 | 7.6 |
| E 11 | 5.4 |
| E 15 | 5.0 |
| E 25 | 10.1 |
| Phenobarbital | 6.9 |

Accordingly, the new compounds under examination increase the bromosulphthaleine excretion to the same or greater level than phenobarbital. The increase of bromosulfophthaleine elimination rate also proves that the detoxicating capacity of the liver is increased.

In an in vivo test, liver tissue removed from animals pre-treated with compounds of the formula (I) as incubated in the presence of bilirubin, in order to determine the UDP-glucuronyltransferase activity of the liver tissues (Adlard, B. P. F., Lester, R. G., Lathe, G. H.: Biochem Pharmacol. 18, 59(1969). The results of this test, compared with those obtained for the untreated controls, are listed in Table 6.

Table 6

| Substance | Conjugated bilirubine μg./g./h. | % |
|---|---|---|
| Control | 25.6 ± 2.1 | |
| E 9 | 36.7 ± 3.2 | + 43 |
| E 11 | 35.7 ± 2.8 | + 40 |
| E 15 | 37.4 ± 3.6 | + 44 |
| E 20 | 35.1 ± 2.6 | + 37 |

As the data of Table 6 shows, both the glucuronization capacity of the liver tissues and the conjugation grade of bilirubin increases upon pre-treatment with the compounds according to the invention.

In investigation of the bilirubin elimination under in vivo conditions on rats pre-treated with E 15 or phenobarbital, respectively, and challenged intravenously with a dosage of 30 mg./kg. of free bilirubin, the following biological halving periods were determined (Krueger, H., Higginson, J.: Proc. Soc. Exp. Biol. Med. 107, 43(1961):

Table 7

| Substance | t½ min |
|---|---|
| Control | 16 |
| E 15 | 7 |
| Phenobarbital | 13 |

It can be stated that E 15 accelerates the elimination of bilirubin in rats to a great extent, this effect being about two times stronger than that of phenobarbital.

The toxicity values of the compounds of the formula (I) are very low, and significantly lower than that of phenobarbital, used as reference substance. Despite its disadvantageous properties, phenobarbital is widely used in the treatment of neonatal jaundice. In order to enable a better comparison, Table 8 indicates the respective dosages in which phenobarbital causes lethal respiration paralysis, while the compound according to the invention are completely innocuous.

Table 8

| Substance | perished animals/tested animals | | | | |
|---|---|---|---|---|---|
| | 40 | 80 | 160 | 320 | 640 mg./kg. |
| Phenobarbital | 0/10 | 0/10 | 4/10 | 9/10 | 10/10 |
| E 9 | 0/10 | 0/10 | 0/10 | 0/10 | 0/10 |
| E 11 | 0/10 | 0/10 | 0/10 | 0/10 | 0/10 |
| E 15 | 0/10 | 0/10 | 0/10 | 0/10 | 0/10 |

As it appears from the data of Table 8, the compounds of the formula (T) are far less toxic than phenobarbital, thus they have far more advantageous therapeutical indices than the reference substance.

The central nervous activities of the compounds according to the invention were examined on mice and rats with the following methods: electroshock (Swinyard, E. A., Browh, W. C., Goodman, L. S.: J. Pharmacol. Exp. Ther. 106, 319 (1952), metrazol spasm (Everett, G. M., Richards, R. K.: J. Pharmacol. Exp. Ther. 81, 402 (1944), thiosemicarbezide spasm (Da Venzo, J. P., Greig, M. E., Cormin, M. A.: Amer. J. Physiol. 201, 833 (1961), strychnine spasm (Kerley, T. L., Richards, A. G., Begley, R. W., Abreu, B. B. Wesver, L. C.: J. Pharmacol. Exp. Ther. 132, 360 (1961), nicotine spasm (Stone, C. A., Mecklenburg, K. L., Torhans, M. L.: Arch. Int. Pharmacodyn. 117, 419 (1958), rotarod test (Kinnard, W. C., Carr, C. J.: J. Pharmacol. Expt. Ther. 121, 354 (1957), physostigmine lethality preventing effect (Nose, T., Kojima, M.: Europ. J. Pharmacol. 10, 83 (1970), yohimbine potentiation effect (Quinton, R. M.: Brit. J. Pharmacol. 21, 51 (1963), and analgesic activity (Bianchi, G., Franceschini, J.: Brit. J. Pharm. Chemother, 9, 280 (1954). As reference substance, phenobarbital was used. Both the compounds under examination and the reference substance were administered orally in dosages of 40, 120, and 150 mg./kg., respectively.

The compounds according to the invention, when administered in the above dosages, were completely ineffective, in the above test, whereas phenobarbital exerted strong antoconvulsive muscle-incoordinating and sedative effects even in a dosage of 40 mg./kg.

Consequently, the new compounds according to the invention have the further advantage over phenobarbital that they are free of central nervous activities.

The new α-substituted benzhydrol derivatives of the formula (I) can be prepared by any method known in the art for the preparation of such compounds. One may proceed, e.g. as follows:

a. a benzophenone of the general formula (II),

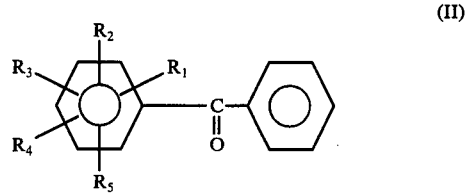

wherein $R_1$, $R_2$, $R_3$, $R_4$ and $R_5$ each have the same meanings as defined above, is reacted with a metalo-organic compound containing ethyl or vinyl groups, preferably with an ethyl magnesium halide or vinyl magnesium halide; or b. to prepare compounds of the general formula (I) wherein Z stands forethyl, a propiophenone of the general formula (III),

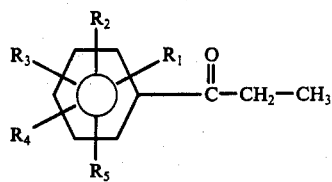

(III)

wherein $R_1$, $R_2$, $R_3$, $R_4$ and $R_5$ each have the same meanings as defined above, is reacted with a phenyl magnesium halide; or c. to prepare compounds of the general formula (I), wherein Z stands for ethyl, a Grignard compound of the general formula (IV)

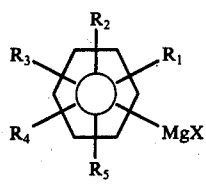

(IV)

wherein $R_1$, $R_2$, $R_3$, $R_4$ and $R_5$ each have the same meanings as defined above and X stands for halogen, is reacted with propiophenone; or d. a compound of the formula (VI),

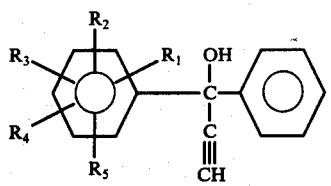

(VI)

wherein $R_1$, $R_2$, $R_3$, $R_4$ and $R_5$ each have the same meanings as defined above, is reduced; or e. a compound of the formula (I) is converted into another compound of the formula (I);

and, if desired, any of the free bases obtained by the above-mentioned process variants is converted into its acid addition salt or quaternary ammonium salt, or a salt of the above compounds is converted into the free basis.

Process variant (a) is carried out preferably by reacting a benzophenone of the formula (II) with an ethyl or vinyl magnesium halide, particularly with ethyl magnesium bromide, ethyl magnesium iodide, vinyl magnesium bromide or vinyl magnesium chloride, in the presence of an anhydrous organic solvent. The Grignard reagent is used in at least equimolar amount. The reaction is carried out preferably in an aprotic organic solvent, e.g. in an alicyclic ether, such as tetrahydrofuran or dioxane, an aliphatic ether, such as ethyleneglycol dimethylether, diethyl ether or di-n-butyl ether, an aliphatic or aromatic hydrocarbon, such as ligroin, benzene, toluene or xylene, or a mixture of these solvents. The reaction is carried out at a temperature ranging from −10° C to the boiling point of the solvent, preferably at −10° to +100° C. When the reaction is over, the Grignard complex is decomposed with a dilute mineral acid, such as hydrochloric or sulfuric acid, or, preferably, with an aqueous solution of ammonium chloride, and the obtained compound of the formula (I) is separated. The product can be purified by distillation or crystallization.

Process variant (b) is carried out preferably by reacting a propiophenone of the formula (III) with at least equimolar amount of a phenyl magnesium halide. The most preferred reagent is phenyl magnesium bromide. The reaction is carried out in an anhydrous organic solvent medium. As solvent, any substance inert towards the reaction, such as an ether or an aliphatic or aromatic hydrocarbon can be used.

According to process variant (c), a Grignard compound of the formula (IV) is reacted with at least an equimolar amount of propiophenone in an anhydrous organic solvent medium. As solvent, preferably an ether, an aliphatic or aromatic hydrocarbon, or a mixture of these solvents is used.

The Grignard compounds of the formula (IV) are prepared from compounds of the formula (V) according to known techniques.

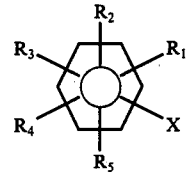

(V)

If the starting compound of the formula (V), wherein $R_1$, $R_2$, $R_3$, $R_4$, $R_5$ and X each have the same meanings as defined above, contains a less reactive halogen atom, an activating reagent, such as ethylene dibromide can be used in the preparation of the Grignard compound. This activating reagent purifies and activates the surface of magnesium, and thus enables it to react with the less reactive halogen atom.

According to process variant (d), the new compounds of the formula (I) can be prepared by the reduction of an ethynyl compound of the formula (VI).

If the reduction is carried out to the uptake of one molar equivalent of hydrogen, in the presence of a catalyst usable to saturate a triple bond partially, compounds of the formula (I), containing a vinyl group as substituent Z, are obtained. For this purpose e.g. palladium-on-calcium carbonate, poisoned with lead acetate (optionally in the presence of quinoline), or Raney-nickel poisoned with zinc acetate (optionally in the presence of piperidine) can be used as a catalyst.

If the reduction is carried out in the presence of Raney-nickel, or palladium or platinum depositioned onto an alkaline earth metal carbonate or sulfate, or activated carbon, a compound of the formula (I), containing ethyl group as substituent Z, is obtained after the uptake of the calculated amount of hydrogen. The reduction is carried out preferably in a solvent medium. As solvent, e.g. a lower aliphatic alcohol, an ether, an ester, or an aliphatic cycloaliphatic or aromatic hydrocarbon can be used. The reduction is carried out preferably at room temperature, under atmospheric pressure.

According to process varient (e), an α-substituted benzhydrol of the formula (I) can be converted into another compound having the formula (I). Thus, for example, when 3-amino-4-chloro-α-ethyl-benzhydrol, a new compound according to the invention, is dehalogenated in methanolic potassium hydroxide in the presence of palladium-on-calcium carbonate, another new compound of the formula (I), 3-amino-α-ethyl-benzhydrol, is obtained. As a further example, 4-cyano-α-ethyl-benzhydrol can be hydrolyzed in methanolic sodium hydroxide to yield 4-carboxy-α-ethyl-benzhydrol.

The compounds of the formula (I-1),

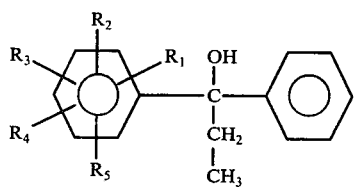

(I-1)

can also be prepared starting from compounds of the formula (I-2).

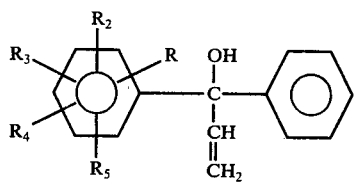

(I-2)

In these formulae $R_1$ and $R_2$ each is hydrogen, halogen, a straight-chained or branched, saturated or unsaturated lower aliphatic hydrocarbon group, a trihalomethyl nitro, nitrile group, an optionally etherified or esterified hydroxy or hydroxyalkyl group, an optionally esterified carboxy group, an optionally acylated amino or lower aminoalkyl group, a lower alkylamino group or an optionally esterified or etherified mercapto group, $R_3$, $R_4$ and $R_5$ each stand for hydrogen, halogen, a straight-chained or branched, saturated or unsaturated lower aliphatic hydrocarbon group or cycloalkyl group, an aralkyl or aryl group, a trihalomethyl group, nitro group, nitrile group, an optionally etherified or esterified hydroxy or hydroxyalkyl group, an optionally esterified carboxy group, an optionally acylated amino or lower aminoalkyl group, a mono- or di-lower alkylamino group forming optionally a ring through a carbon, nitrogen or oxygen atom, a lower alkylamino-mono- or di-lower alkyl group, forming optionally a ring through a carbon, nitrogen or oxygen atom, or an optionally esterified or etherified mercapto group.

The preparation of α-ethyl-benzhydrols starting from the appropriate α-vinyl compounds was not described so far in the literature. According to the process of the invention, compounds of the formula (I-1) can be obtained in practically quantitative yields by reducing the appropriate compounds of the formula (I-2). The reduction can be carried out e.g. by catalytic hydrogenation, using platinum, palladium, ruthenium or Raney-nickel as catalyst. The reaction is carried out preferably in the presence of a solvent inert towards the reaction, such as in an aliphatic, cycloaliphatic or aromatic hydrocarbon, an ether, an ester, a lower alcohol, or a mixture thereof. The hydrogenation can be carried out under atmospheric or super-atmospheric pressures, preferably under a pressure not higher than 5 atm., and at a temperature ranging from 20° C to the boiling point of the system. The reaction is carried out preferably at room temperature, under atmospheric pressure. When the calculated amount of hydrogen is absorbed, the catalyst is removed by filtration, the product is isolated, and purified e.g. by distillation or crystallization. The reduction can also be carried out by hydrogen transfer, i.e. using a hydrogen donating agent, such as cyclohexene, as hydrogen source. This reaction is carried out in cyclohexene or in a mixture of cyclohexene and an organic solvent inert towards the reaction, at a temperature ranging from 20° C to the boiling point of the system, in the presence of a metal catalyst, e.g. palladium or Raney-nickel.

If desired, the compounds of the formulae (I) and (I-1) can be converted into their acid addition salts or quaternary ammonium salts by methods well known in the art. Quaternarization can be carried out using a straight-chained or branched lower alkyl or alkenyl halide or benzyl halide, or a straight-chained alkyl sulfate. The reaction is carried out in a solvent, preferably acetone, ethanol or acetonitrile, at the boiling temperature of the solvent. If higher temperature are to be maintained, the reaction can be carried out under pressure.

The compounds of the formulae (II) and (III), used as starting substances, can be prepared by methods well known in the art, e.g. by the Friedel-Crafts type ketone synthesis.

The compounds of the formula (IV) can be prepared from the appropriate compounds of the formula (V), by the well-known method of Grignard reagent formation.

The compounds of the formula (VI), used as starting substances, can be prepared by subjecting the corresponding substituted benzophenones to ethynylation.

The pharmacologically active compounds according to the invention can be used in the therapy in the form of pharmaceutical compositions. These compositions, suitable for enteral, parenteral or topical administration, contain the new compounds of the formula (I) together with pharmaceutically acceptable organic or mineral solid or liquid carriers. Only those carriers can be used which do not enter into reaction with the active ingredient. Such carriers are e.g. water, alcohol, gelatine, propylene glycol, vegetable oils, cholesterol, starch, lactose, talc, gum, magnesium stearate, etc. The compositions can be sterilized, if desired.

The pharmaceutical compositions may contain auxiliary agents, such as preserving, stabilizing, wetting, or emulsifying agents, dissolution aids, salts or buffers to adjust the osmotic pressure, etc. The compounds of the formula (I) may be present in combination with other pharmaceutically valuable substances. The pharmaceutical compositions can be prepared by methods well known in the art. The injectable preparations are produced e.g. by dissolving an acid addition or quaternary salt of the active agent in pyrogen-free physiological saline solution or in bidistilled water, sterilizing the solution, if necessary, and pouring it into vials under sterile conditions.

The invention is illustrated in greater detail by the aid of the following Examples.

EXAMPLE 1

2-Amino-5-chloro-α-ethyl-benzhydrol

Ethyl magnesium bromide is prepared from 9.7 g. of magnesium turnings and 38.15 g. of ethyl bromide in 115 ml. of dry ether. A solution of 23.2 g. of 2-amino--5-chloro-benzophenone in 350 ml. of dry ether is added dropwise to the cooled Grignard solution, taking care that the temperature should not rise above −5° C. After the addition the reaction mixture is stirred at 0° C for 30 minutes. The progress of the reaction can be monitored by thin layer chromatography. When the reaction is over, the mixture is poured onto a solution of ammonium chloride in ice water. The etheral phase is separated, washed with aqueous sodium chloride solution and then with water until neutral, dried over sodium sulfate, and the solvent is distilled off. The obtained 18.3 g. of crude 2-amino-5-chloro-α-ethyl-benzhydrol are recrystallized from n-heptane, to yield a purified product melting at 91.5°–92° C.

Analysis: Calculated for $C_{15}H_{16}ClNO$: C, 68.83%; H, 6.16%; Cl, 13.55%; N, 5.35%. Found C, 68.70%; H, 6.21%; Cl, 13.52%; N, 5.18%.

Characteristic I.R absorption bands: 700, 760, 820, 885, 3200, 3280, 3400 cm$^{-1}$.

UV spectrum: $\lambda_{max.}^{EtOH}$ 215, 250, 370 nm.

Similarly can be prepared the following compounds by the proper selection of the starting substances:

4-Phenyl-α-ethyl-benzhydrol

Melting point: 100°–101° C

Analysis: Calculated for $C_{21}H_{20}O$: C, 87.46%; H, 6.99%. Found: C, 87,51%; H, 7.08%.

Characteristic I.R. absorption bands: 700, 765, 775, 835, 3560 cm$^{-1}$.

U.V. spectrum: $\lambda_{max.}^{EtOH}$ 257 nm.

4-Cyclopropyl-α-ethyl-benzhydrol

Boiling point: 180°–182° C/0.2 mmHg.

Analysis: Calculated for $C_{20}H_{24}O$: C, 85.66%; H, 8.63%. Found: C, 85.61%; H, 8.42%.

Characteristic I.R. absorption bands: 700, 760, 830, 2880, 2960, 3480, 3570 cm$^{-1}$.

U.V. spectrum: $\lambda_{max.}^{EtOH}$ 222, 254, 259, 265, 273 nm.

3-Amino-4-piperidino-α-ethyl-benzhydrol

Melting point: 103°–104° C

Analysis: Calculated for $C_{20}H_{26}N_2O$: C, 77.38%; H, 8.44%; N, 9.03%. Found: C, 77.49%; H, 7.70%; N, 8.95%.

Characteristic IR absorption bands: 705, 760, 805, 880, 2820, 2940, 3300, 3370, 3460, 3580 cm$^{-1}$.

UV spectrum: $\lambda_{max.}^{EtOH}$ 221, 296 cm.

4-Cyano-α-ethyl-benzhydrol

Melting point: 81.5°–82.5° C.

Analysis: Calculated for $C_{16}H_{15}NO$: C, 80.98%; H, 6.37%; N, 5.90%. Found: C, 81.04%; H, 6.24%; N, 6.00%.

Characteristic IR absorption bands: 705, 760, 840, 2240, 3540 cm$^{-1}$.

UV spectrum: $\lambda_{max.}^{EtOH}$ 242 nm.

EXAMPLE 2

4-Hydroxy-α-vinyl-benzhydrol

A solution of 20 g. of 4-hydroxy-benzophenone in 180 ml. of dry ether is added, within about 30 minutes, to a 0° C solution of 184 ml. of a 3.4 molar tetrahydrofuran solution of vinyl magnesium chloride, and the reaction mixture is stirred at the same temperature for additional 1 hour. The mixture is allowed to stand at room temperature overnight. Thereafter the mixture is poured onto ice water containing ammonium chloride. The etheral phase is separated, washed with water until neutral, dried over anhydrous magnesium sulfate, and the solvent is evaporated. 22.6 g. of crude 4-hydroxy-α-vinyl-benzhydrol are obtained. After recrystallization from a mixture of ethyl acetate and n-hexane, the product melts at 104°–105° C.

Analysis: Calculated for $C_{15}H_{14}O_2$: C, 79.62%; H, 6.24%. Found: C, 79.55%; H, 6.18%.

Characteristic IR absorption bands: 700, 770, 830, 1640, 3280, 3410 cm$^{-1}$.

UV spectrum: $\lambda_{max.}^{EtOH}$ 228, 278 nm.

EXAMPLE 3

2-Methyl-α-ethyl-benzhydrol

Phenyl magnesium bromide is prepared from 14.5 g. of magnesium turnings and 80 g. of bromobenzene in 200 ml. of dry ether. The Grignard solution is cooled to −5° C, and a solution of 71. g. of 2-methyl-propiophenone in 100 ml. of ether is added under vigorous stirring. The mixture is refluxed for 15 minutes, thereafter cooled, and the Grignard complex is decomposed with an aqueous solution of ammonium chloride under cooling. The ethereal phase is separated, washed with water until neutral, and dried over anhydrous magnesium sulfate. The solvent is evaporated, and the residue is subjected to fractional distillation. Thus, 84.7 g. of 2-methyl-α-ethyl-benzhydrol are obtained; b.p.: 109°–113° C/O.

Analysis: Calculated for $C_{16}H_{18}O$: C, 84.91%; H, 8.02%. Found: C, 84.76%; H, 7.89%.

Characteristic IR absorption bands: 700, 750, 770, 3500 cm$^{-1}$.

UV spectrum: $\lambda_{max.}^{EtOH}$ 221, 259, 265, 272 nm.

Similarly are prepared the following compounds by the proper selection of the starting substances.

4-Benzyl-α-ethyl-benzhydrol

Boiling point: 172°–176° C/0.1 mmHg.

Analysis: Calculated for $C_{22}H_{22}O$: C, 87.37%; H, 7.33%. Found: C, 87.56%; H, 7.34%.

Characteristic IR absorption bands: 700, 745, 760, 850, 3460, 3570 cm$^{-1}$.

UV spectrum: $\lambda_{max.}^{EtOH}$ 224, 254 nm.

4-Methylthio-α-ethyl-benzhydrol

Boiling point: 148°–152° C/0.1 mmHg.

Analysis: Calculated for $C_{16}H_{18}OS$: C, 74.37%; H, 7.02%; S, 12.41%. Found C, 74.19%; H, 7.13% S, 12.32%.

EXAMPLE 4

3-Trifluoromethyl-α-ethyl-benzhydrol

A solution of 37.5 g. of propiophenone in 200 ml. of dry ether is added dropwise to a −10° C Grignard solution prepared from 13.6 g. of magnesium turnings and 126 g. of 3-trifluoromethyl-bromobenzene in 182 ml. of dry ether. The reaction mixture is stirred at 0° C for 30 minutes, thereafter refluxed for 1 hour. The mixture is cooled to 0° C, and the Grignard complex is decomposed with a 10% aqueous ammonium chloride solution. The etheral phase is separated, washed until neutral, and dried over anhydrous sodium sulfate. The solvent is evaporated, and the residual oil is subjected to fractional distillation in vacuo. This way 57.3 g. of 3-trifluoromethyl-α-ethyl-benzhydrol are obtained; b.p.: 106°–108° C/0.03 mmHg.

Analysis:
Calculated for $C_{16}H_{15}F_3O$:
C, 68.56%; H, 5.39%; F, 20.34%.
Found: C, 68.55%; H, 5.42%; F, 20.18%.

Characteristic IR absorption bands: 700, 760, 800, 1080, 1120, 1170, 1320, 3400 cm$^{-1}$.

UV spectrum: $\lambda_{max}^{EtOH}$ 259, 265, 271 nm.

Similarly are prepared the following compounds by the proper selection of the starting substances:

2-Trifluoromethyl-α-ethyl-benzhydrol

Boiling point: 91°–94° C/0.15 mmHg.

Analysis: Calculated for $C_{16}H_{15}F_3O$: C, 68.56%; H, 5.39%; F, 20.34%. Found: C, 68.64% H, 5.44%; F, 20.27%.

Characterisitc IR absorption bands: 700, 750, 1000, 1130, 1160, 1310, 3500 cm$^{-1}$.

UV spectrum: $\lambda_{max}^{EtOH}$ 215, 260, 266, 273 nm.

4-Trifluoromethyl-α-ethyl-benzhydrol

Boiling point: 102°–103° C/0.12 mmHg.

Analysis: Calculated for $C_{16}H_{15}F_3O$: C, 68.56%; H, 5.39%; F, 20.34%. Found: C, 68.61%; H, 5.55%; F, 20.28%.

Characteristic IR absorption bands: 700, 760, 835, 1070, 1120, 1170, 1325, 3400 cm$^{-1}$.

UV spectrum: $\lambda_{max}^{EtOH}$ 219, 253, 259, 264 nm.

2,3,4,5,6-Pentafluoro-α-ethyl-benzhydrol

Boiling point: 82°–84° C/0.15 mmHg.

Analysis: Calculated for $C_{15}H_{11}F_5O$: C, 59.61%; H, 3.67%; F, 31.43%; Found: C, 59.80%; H, 3.38%; F, 31.50%.

Characteristic IR absorption bands: 700, 760, 990, 3400 cm$^{-1}$.

UV spectrum: $\lambda_{max}^{EtOH}$ 259, 264 nm.

EXAMPLE 5

2-Fluoro-α-vinyl-benzhydrol 22.6 g. 2-fluoro-α-ethynyl-benzhydrol and 0.74 g. of zinc acetate dihydrate are dissolved in a mixture of 260 ml. of methanol and 10 ml. of piperidine, and 4.4 g. of Raney-nickel catalyst are added to the mixture. The reaction mixture is hydrogenated at room temperature under atmospheric pressure until the uptake of the calculated amount of hydrogen. Thereafter the catalyst is filtered off, and the solvent is evaporated in vacuo. The residue is dissolved in benzene, and the solution is washed with water in order to remove zinc acetate. The benzene phase is dried over anhydrous magnesium sulfate, filtered, and evaporated. The residual oil is distilled at 0.05 mmHg. 21.4 g. of colorless, oily 2-fluoro-α-vinyl-benzhydrol are obtained; b.p.: 91°–93° C/0.05 mmHg.

Analysis: Caclculated for $C_{15}H_{13}FO$: C, 78.92%; H, 5.74%; F, 8.32%. Found: C, 79.94%; H, 5.81%; F, 8.18%.

Characteristic IR absorption bands: 705, 765, 770, 1220, 3460, 3580 cm$^{-1}$.

UV spectrum: $\lambda_{max}^{EtOH}$ 263, 269 nm.

Similarly are prepared the following compounds by the proper selection of the starting substances:

2,4-dichloro-α-vinyl-benzhydrol
3-iodo-α-vinyl-benzhydrol
3-chloro-α-vinyl-benzhydrol
2-chloro-α-vinyl-benzhydrol
4-fluoro-α-vinyl-benzhydrol
4-chloro-α-vinyl-benzhydrol
3,4-dichloro-α-vinyl-benzhydrol
3,4,5-trimethoxy-α-vinyl-benzhydrol
4-tert.-butyl-α-butyl-benzhydrol
4-bromo-α-vinyl-benzhydrol
3-amino-4-chloro-α-vinyl-benzhydrol and also the following further similar compounds.

4-(β-Diethylaminoethoxy)-α-vinyl-benzhydrol

Boiling point: 168°–172° C/0.05 mmHg.

Analysis: Calculated for $C_{21}H_{27}NO_2$: C, 77.50%; H, 8.36%; N, 4.30%. Found: C, 77.49%; H, 8.21%; N, 4.41%.

Characterisitc IR absorption bands: 705, 765, 835, 1050, 1250, 2820, 3100 to 3500 cm$^{-1}$.

UV spectrum: $\lambda_{max}^{EtOH}$ 229, 276, 283 nm.

4-n-Butyl-α-vinyl-benzhydrol

Boiling point: 136°–138° C/0.1 mmHg.

Analysis: Calculated for $C_{19}H_{22}O$: C, 85.67%; H, 8.33%. Found: C, 85.86%; H, 8.21%.

Characteristic IR absorption bands: 705, 765, 835, 2860, 2880, 2940, 2970, 3460, 3570 cm$^{-1}$.

UV spectrum: $\lambda_{max}^{EtOH}$ 260, 265 nm.

2,4-Dimethoxy-α-vinyl-benzydrol.

Melting point 52°–53° C.

Analysis: Calculated for $C_{17}H_{18}O_3$: C, 75.53%; H, 6.71%. Found: C, 75.72%; H, 6.88%.

Characteristic IR absorption bands: 705, 765, 820, 860, 1030, 1210, 3560 cm$^{-1}$.

UV spectrum: $\lambda_{max}^{EtOH}$ 278, 283 nm.

EXAMPLE 6

2,4-Dichloro-α-ethyl-benzhydrol 0.48 g. of 10% palladium-on-carbon catalyst are added to a solution of 19.4 g. of 2,4-dichloro-α-ethynyl-benzhydrol in 200 ml. of benzene, and the mixture is hydrogenated until the absorption of the calculated amount of hydrogen (about 60 minutes). Thereafter the catalyst is removed by filtration, and the solvent is evaporated. The obtained 16.1 g. of crude product is distilled in vacuo, to yield pure 2,4-di-chloro-α-ethyl-benzhydrol, b.p.: 136°–138° C/0.1 mmHg.

Analysis: Calculated for $C_{15}H_{14}Cl_2O$: C, 64.07%; H, 5.02%; Cl, 25.22%. Found: C, 64.21%; H, 5.13%; Cl, 25.41%.

Characteristic IR absorption bands: 700, 770, 880, 825, 1050, 1095, 3500 cm$^{-1}$.

UV spectrum: $\lambda_{max}^{EtOH}$ 254, 259, 264, 280 nm.

Similarly are prepared the following compounds from the appropriate starting substances:

3-Iodo-α-ethyl-benzhydrol

Boiling point: 136°–139° C/0.04 mmHg.

Analysis: Calculated for $C_{15}H_{15}IO$: C, 53.26%; H, 4.47%; I, 37.52%. Found: C, 53.11%; H, 4.71%; I, 37.44%.

Characteristic IR absorption bands: 700, 765, 785, 3400 cm$^{-1}$.

UV spectrum: $\lambda_{max}^{EtOH}$ 253, 258 nm.

3-Chloro-α-ethyl-benzhydrol

Boiling point: 124°–125° C/0.02 mmHg.

Analysis: Calculated for $C_{15}H_{15}ClO$: C, 73.02%; H, 6.13%; Cl, 14.37%. Found: C, 72.87%; H, 6.28%; Cl, 14.36%.

Characteristic Ir absorption bands: 695, 700, 740, 785, 1075, 3400 cm$^{-1}$.

UV spectrum: $\lambda_{max}^{EtOH}$ 255, 259, 274 nm.

2-Fluoro-α-ethyl-benzhydrol

Melting point: 52.5°–53.5° C
Analysis: Calculated for $C_{15}H_{15}FO$: C, 78.23%; H, 6.57%; F, 8.25%. Found: C, 78.39%; H, 6.75%; F, 8.25%.
Characteristic IR absorption bands: 700, 760, 770, 3500 cm$^{-1}$.
UV spectrum: $\lambda_{max}^{EtOH}$ 262, 268 nm.

2-Chloro-α-ethyl-benzhydrol

Melting point: 50.5°–51.5° C
Analysis: Calculated for $C_{15}H_{15}ClO$: C, 73.02%; H, 6.13%; Cl, 14.37%. Found: C, 73.00%; H, 6.21%; Cl, 14.39%.
Characteristic IR absorption bands: 700, 750, 760, 3350 cm$^{-1}$.
UV spectrum: $\lambda_{max}^{EtOH}$ 254, 259, 265 nm.

4-Fluoro-α-ethyl-benzhydrol

Boiling point: 135°–137° C/5 mmHg.
Analsyis: Calculated for $C_{15}H_{15}FO$: C, 78.23%; H, 6.57%; F, 8.25%. Found: C, 78.26%; H, 6.29%; F, 8.42%.
Characteristic IR absorption bands: 700, 760, 830, 3500 cm$^{-1}$.
UV spectrum: $\lambda_{max}^{EtOH}$ 260, 265, 271 nm.

4-Chloro-α-ethyl-benzhydrol

Boiling point: 153°–155° C/0.3 mmHg.
Analysis:
Calculated for $C_{15}H_{15}ClO$: C, 73.02%; H, 6.13%; Cl 14.37%. Found: C, 72.84%; H, 5.84%; Cl, 14.49%.
Characteristic IR absorption bands: 700, 765, 830, 3500 cm$^{-1}$.
UV spectrum: $\lambda_{max}^{EtOH}$ 223, 254, 259, 275 nm.

3,4-Dichloro-α-ethyl-benzhydrol

Boiling point: 140°–142° C/0.1 mmHg.
Analysis: Calculated for $C_{15}H_{14}Cl_2O$: C, 64.07%; H, 5.02%; Cl, 25.22%. Found: C, 64.22% H, 5.13%; Cl, 25.11%.
Characteristic IR absorption bands: 700, 755, 825, 880, 1070, 3400 cm$^{-1}$.
UV spectrum: $\lambda_{max}^{EtOH}$ 258, 264, 281 nm.

EXAMPLE 7

3,4,5-Trimethoxy-α-ethyl-benzhydrol 28.3 g. of 3,4,5-trimethoxy-α-ethynyl-benzhydrol are dissolved in 227 ml. of ethanol, the solution is poured into a hydrogenating vessel, and shaken with 11 g. of Raney-nickel. The mixture is reduced until the uptake of the calculated amount of hydrogen. Thereafter the catalyst is filtered off, and the solvent is evaporated in vacuo. The solid residue is recrystallized from n-heptane to yield 23.6 g. of 3,4,5-trimethoxy-α-ethyl-benzhydrol, m.p.: 123°–124° C.
Analysis: Calculated for $C_{18}H_{22}O_4$: C, 71.50%; H, 7.33%. Found: C, 71.41%; H, 7.18%.
Characteristic IR absorption bands: 705, 760, 835, 855, 1010, 1130, 1140, 3460 cm$^{-1}$.
UV spectrum: $\lambda_{max}^{EtOH}$ 218, 268, 273 nm.
Similarly are prepared the following compounds from the appropriate starting substances:

4-tert-Butyl-α-ethyl-benzhydrol

Boiling point: 148°–150° C/0.4 mmHg.
Analysis: Calculated for $C_{19}H_{24}O$: C, 85.02%; H, 9.01%. Found: C, 84.84%; H, 9.14%.
Characteristic IR absorption bands: 700, 765, 830, 3450 cm$^{-1}$.
UV spectrum: $\lambda_{max}^{EtOH}$ 258, 263 nm.

4-(β-Diethylaminoethoxy)-α-ethyl-benzhydrol

The physical constants of this compound are the same as given in Example 14.

EXAMPLE 8

4-Carboxy-α-ethyl-benzhydrol

A mixture of 24 g. of 4-cyano-α-ethyl-benzhydrol and 230 ml. of 10% methanolic sodium hyroxide solution is refluxed under nitrogen atmosphere. The hydrolysis takes place quantitatively within about 3 to 4 hours, and the progress of the reaction can be monitored easily by thin layer chromatography. When the reaction is over the mixture is evaporated under reduced pressure. The residue is suspended in benzene, and an aqueous solution of citric acid is added under vigorous stirring in order to liberate 4-carboxy-α-ethyl-benzhydrol from its sodium salt. The benzene phase is separated, washed with water, and dried over anhydrous magnesium sulfate. The solvent is evaporated under reduced pressure, and the solid residue is crystallized. This way 20.8 g. of 4-carboxy-α-ethyl-benzhydrol are obtained m.p.: 128.5°–129.5° C.
Analysis: Calculated for $C_{16}H_{16}O_3$: C, 74.98%; H, 6.29%. Found: C, 75.12%; H, 6.41%.
Characteristic IR absorption bands: 700, 850, 1670, 2400 to 3200, 3540 cm$^{-1}$.
UV spectrum: $\lambda_{max}^{EtOh}$ 243 nm.

EXAMPLE 9

4-Aminomethyl-α-ethyl-benzhydrol 24 g. of 4-cyano-α-ethyl-benzhydrol are dissolved in 192 ml. of ethanol, and 48 ml. of a 25% aqueous ammonium hydroxide solution and 9.6 g. of Raney-nickel are added. The reaction mixture is hydrogenated at 50° C. After the uptake of the theoretical amount of hydrogen the catalyst is filtered off, and the clear filtrate is evaporated to dryness under reduced pressure. The solid residue is recrystallized from a mixture of n-heptane and benzene to yield 17 g. of 4-aminomethyl-α-ethyl-benzhydrol melting at 97.5°–98.5° C.
Analysis: Calculated for $C_{16}H_{19}NO$: C, 79.63%; H, 7.94%; N, 5.80%. Found: C, 79.44%; H, 8.12%; N, 5.91%.
Characteristic Ir absorption bands: 705, 770, 815, 2700 to 3500, 3300, 3370 cm$^{-1}$.
UV spectrum: $\lambda_{max}^{EtOH}$ 221, 260, 264 nm.

EXAMPLE 10

3-Amino-α-ethyl-benzhydrol 2.6 g. of 3-amino-4-chloro-α-ethyl-benzhydrol are dissolved in methanol containing 3.9 g. of potassium hydroxide. 8.7 g. of an 5% palladium-on-calcium carbonate catalyst are added to the mixture, and the suspension is hydrogenated at room temperature under atmospheric pressure. After the uptake of the calculated amount of hydrogen the catalyst is filtered off and washed with 15 ml. of methanol. The filtrate and the wash are combined and concentrated to 40 ml. under reduced pressure. The product is precipitated from the concentrate with water. The solids are filtered off, washed until neutral, and dried until constant weight. The crude product is recrystallized from alcohol to yield 1.7 g. of 3-amino-α-ethyl-benzhydrol, metling at 92°-93° C.

Analysis: Calculated for $C_{15}H_{17}NO$: C 79.26%; H 7.54%; N 6.16%. Found: C 79.28%; H 7.71%; N 5.99%.

Characteristic IR absorption bands: 705, 710, 760, 780, 3300, 3320, 3400, 3480 cm$^{-1}$.

UV spectrum: $\lambda_{max.}{}^{EtOH(HCl)}$ 253; 260 nm.

EXAMPLE 11

4-Bromo-α-ethyl-benzhydrol 0.6 g. of 10% palladium-on-carbon are added to a solution of 29 g. of 4-bromo-α-vinyl-benzhydrol in 300 ml. of benzene, and the mixture is hydrogenated at room temperature under atmospheric pressure. After the uptake of the calculated amount of hydrogen the catalyst is filtered off, and the benzene is evaporated from the clear filtrate under reduced pressure. 25 g. of clear, viscous oil, boiling at 140° C/0.8 mmHg. are obtained as residue.

Analysis: Calculated for $C_{15}H_{15}BrO$: C 61.87%; H 5.19%; Br 27.44%. Found: C 62.06%; H 5.25%; Br 27.45%.

Characteristic IR absorption bands: 700, 760, 820, 3500 cm$^{-1}$.

UV spectrum: $\lambda_{max.}{}^{EtOH}$ 221, 253, 259, 259 nm.

EXAMPLE 12

α-Ethyl-benzhydrol

A mixture of 21 g. of α-vinyl-benzhydrol and 84 ml. of cyclohexane is refluxed in the presence of palladium catalyst. When the reaction is over, as evidenced by thin layer chromatography, the mixture is cooled, the catalyst is filtered off, and the filtrate is evaporated under reduced pressure. 21.2 g. of crystalline α-ethyl-benzhydrol, melting at 93°-94° C, are obtained as residue.

Analysis: Calculated for $C_{15}H_{16}O$: C 84.87%; H 7.60%. Found: C 84.81%; H 7.88%.

Characteristic IR bands: 700, 710, 760, 770, 3500 cm$^{-1}$.

UV spectrum: $\lambda_{max.}{}^{EtOH}$ 253, 258, 264, 268 nm.

EXAMPLE 13

2,5-Dimethyl-α-ethyl-benzhydrol 10 g. of 5% palladium-on-calcium-carbonate catalyst are added to a solution of 94.5 g. of 2,5-dimethyl-α-ethynyl-benzhydrol in 900 ml. of methanol, and the mixture is hydrogenated until the uptake of the calculated amount of hydrogen (about 30 to 40 minutes). The catalyst is filtered off, the filtrate is evaporated, and the obtained crystalline residue is recrystallized from n-heptane. This way 80.7 g. of 2,5-dimethyl-α-ethyl-benzhydrol are obtained, m.p.: 38°-39° C.

Analysis: Calculated for $C_{17}H_{20}O$: C 84.95%; H 8.39%. Found: C 85.10%; H 8.59.

Characteristic IR absorption bands: 700, 760, 820, 880, 3500 cm$^{-1}$.

UV spectrum: $\lambda_{max.}{}^{EtOH}$ 270, 278 nm.

The above compound was also prepared from 2,5-dimethyl-benzophenone as described in Example 1, and from 2,5-dimethyl-α-vinyl-benzhydrol as described in Example 11. The physical constants of the obtained products are identical with those listed above.

EXAMPLE 14

4-(β-Diethylaminoethoxy)-α-ethyl-benzhydrol

Ethyl magnesium bromide is prepared from 3.88 g. of magnesium turnings and 17.44 g. of ethyl bromide in 60 ml. of anhydrous ether, the Grignard solution is cooled to −10° C, and a solution of 24 g. of 4-(β-diethylamino-ethoxy)-benzophenone in 120 ml. of dry ether is added dropwise. The reaction mixture is stirred vigorously, warmed to 0° C, stirred for 30 minutes at this temperature, and finally refluxed for 15 minutes. When the reaction is over — which can be easily monitored by thin layer chromatography —, the mixture is poured onto ice water containing ammonium chloride. The etheral phase is separated, and the aqueous phase is extracted with 60 ml. of ether in two portions. The etheral solutions are combined, washed until neutral, dried over anhydrous magnesium sulfate, and evaporated to dryness. The solid residue is recrystallized from ethanol. This way 18.1 g. of 4-(β-diethyl-aminoethoxy)-α-ethyl-benzhydrol are obtained, melting at 58°-59° C.

Analysis: Calculated for $C_{21}H_{29}NO_2$: C 77.02%; H 8.93%; N 4.28%. Found: C 77.04%; H 9.17%; N 4.11%.

Characteristic IR absorption bands: 700, 755, 830, 1030, 1250, 3150 cm$^{-1}$.

UV spectrum: $\lambda_{max.}{}^{EtOH}$ 228, 275, 282 nm.

This compound was also prepared with practically quantitative yield by reducing 4-(β-diethylaminoethoxy)-α-vinyl-benzhydrol as described in Example 11. The physical constants of the obtained product are identical with those listed above.

An ethanol solution of 4-(β-diethylaminoethoxy)-α-ethyl-benzhydrol is treated with an ethanol solution of equimolar amount of fumaric acid. The solution is cooled to −15° C, and diluted with ether. The separated hydrogen fumarate is filtered off, washed with ether, and dried. The obtained product, 4-(β-diethylaminoethoxy)-α-ethyl-benzhydrol hydrogen fumarate melts at 108.5°-109.5° C.

Similarly are prepared the following compounds from the appropriate starting substances:

4-n-Butyl-α-ethyl-benzhydrol

Boiling point: 144°-145° C/0.1 mmHg.

Analysis: Calculated for $C_{19}H_{24}O$: C 85.02%; H 9.01%. Found: C 84.82%; H 9.24%.

Characteristic IR absorption bands: 700, 760, 830, 3500 cm$^{-1}$.

UV spectrum: $\lambda_{max.}{}^{EtOH}$ 258, 264, 272 nm.

2-Methoxy-α-ethyl-benzhydrol

Melting point: 62°-63° C.

Analysis: Calculated for $C_{16}H_{18}O_2$: C 79.31%; H 7.49%. Found: C 79.50%; H 7.27%.

Characteristic Ir absorption bands: 700, 745, 760, 1020, 1240, 3500 cm$^{-1}$.

UV spectrum: $\lambda_{max.}{}^{EtOH}$ 228, 275, 282 nm.

EXAMPLE 15

4-(β-Diethylaminoethoxy)-α-ethyl-benzhydrol ethobromide 16.3 g. of 4(β-diethylaminoethoxy)-α-ethyl-benzhydrol are dissolved in 250 ml. of acetonitrile, and 14 ml. of ethyl bromide are added. The mixture is refluxed for 2 hours, then allowed to stand overnight. The solution is evaporated under reduced pressure, and the solid residue is recrystallized from acetone. This way 17.4 g. of crystalline 4-(β-diethylaminoethoxy)-α-ethyl-benzhydrol ethobromide are obtained, m.p.: 113° C.

EXAMPLE 16

3-Amino-4-chloro-α-ethyl-benzhydrol

This compound is prepared from 3-amino-4-chlorobenzophenone as described in Example 1, or by reducing 3-nitro-4-chloro-α-ethyl-benzhydrol as described in Example 7. The product melts at 103° C.

Analysis: Calculated for $C_{15}H_{16}ClNO$: C 68.83%; H 6.16%; Cl 13.55%; N 5.35%. Found: C 69.01%; H 6.18%; Cl 13.68%; N 5.17%.

Characteristic IR absorption bands: 700, 760, 800, 870, 3220, 3320 cm$^{-1}$.

UV spectrum: $\lambda_{max.}^{EtOH}$ 218, 297 nm.

EXAMPLE 17

2-(N-Benzoyl)-amino-5-chloro-α-ethyl-benzhydrol 5.2 g. of 2-amino-5-chloro-α-ethyl-benzhydrol, dissolved in 100 ml. of dry acetone, are acylated with 2.82 g. of benzoyl chloride in the presence of 3.4 g. of anhydrous sodium hydrocarbonate. When the reaction is over, the separated inorganic salt is filtered off, and the filtrate is evaporated under reduced pressure. The residue is recrystallized from alcohol. This way 5 g. of 2-(N-benzoyl)-amino-5-chloro-α-ethyl-benzhydrol are obtained, melting at 188–189° C.

Analysis: Calculated for $C_{22}H_{20}ClNO_2$: C 72.22%; H 5.51%; Cl 9.69%; N 3.83%. Found: C 72.18%; H 5.68%; Cl 9.49%; N 3.91%.

Characteristic IR absorption bands: 700, 770, 835, 870, 1300, 1540, 1650, 3250 cm$^{-1}$.

UV spectrum: $\lambda_{max.}^{EtOH}$ 218, 277 nm.

What we claim is:

1. A compound of the formula:

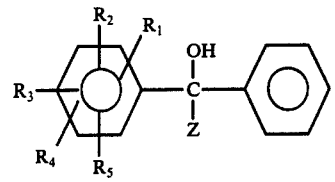

wherein
Z is ethyl,
$R_1$, and $R_2$ and $R_3$, are hydrogen,
$R_4$ is hydrogen, lower alkyl, lower alkenyl, trihalomethyl, cyclopentyl, benzyl or phenyl, and
$R_5$ is lower alkyl or provided that where $R_1$, $R_2$, $R_3$ and $R_4$ each is hydrogen, $R_5$ is not methyl attached to the 4-position of the benzene ring, or a pharmaceutically acceptable acid addition or quaternary ammonium salt of the compound of said formula.

2. A compound selected from the group which consists of:
4-Phenyl-α-ethyl-benzhydrol,
4-Cyclopentyl-α-ethyl-benzhydrol,
2-Methyl-α-ethyl-benzhydrol,
4-Benzyl-α-ethyl-benzhydrol,
3-Trifluoromethyl-α-ethyl-benzhydrol,
2-Trifluoromethyl-α-ethyl-benzhydrol,
4-Trifluoromethyl-α-ethyl-benzhydrol,
4-n-Butyl-α-vinyl-benzhydrol,
4-tert.Butyl-α-ethyl-benzhydrol,
2,5-Dimethyl-α-ethyl-benzhydrol, and
4-n-Butyl-α-ethyl-benzhydrol 3. A compound of the following formula:

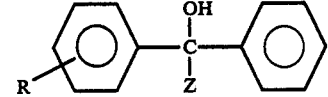

wherein
R is trihalomethyl and
Z is ethyl.

4. 3-trifluoromethyl-α-ethyl benzhydrol.

* * * * *